United States Patent [19]

Umezawa et al.

[11] Patent Number: 4,567,165

[45] Date of Patent: Jan. 28, 1986

[54] N-METHANESULFONIC ACID DERIVATIVES OF 3-DEMETHOXYISTAMYCIN B

[76] Inventors: Hamao Umezawa, Tokyo; Shinichi Kondo, Yokohama, both of Japan; Zaidan Hojin Biseibutsu Kagaku Kenkyu Kai, 03, Japan

[21] Appl. No.: 608,213

[22] Filed: May 8, 1984

[51] Int. Cl.$^4$ .................. A61K 31/71; C07H 15/22
[52] U.S. Cl. ..................... 514/36; 536/13.7; 536/16.1; 536/16.8
[58] Field of Search ............ 536/13.7, 16.1, 16.8; 424/180; 514/36

[56] References Cited

U.S. PATENT DOCUMENTS

| | | | |
|---|---|---|---|
| 4,091,202 | 5/1978 | Umezawa et al. | 536/13.7 |
| 4,296,106 | 10/1981 | Umezawa et al. | 536/16.8 |
| 4,382,926 | 5/1983 | Umezawa et al. | 536/16.1 |
| 4,472,388 | 9/1984 | Umezawa et al. | 536/16.1 |
| 4,479,943 | 10/1984 | Umezawa et al. | 536/16.1 |

*Primary Examiner*—Johnnie R. Brown
*Assistant Examiner*—Elli Peselev
*Attorney, Agent, or Firm*—Larson and Taylor

[57] ABSTRACT

As new semi-synthetic antibiotic derivatives are provided N-methanesulfonic acid derivatives of 3-demethoxyistamycin B which are less toxic than the parent 3-demethoxyistamycin B but retain usefully high antibacterial activity of the parent antibiotic. The new derivatives are produced by a method of N-sulfomethylation where 3-demethoxyistamycin B is reacted with an aldehyde such as paraformaldehyde and sulfurous acid or sulfite reagent.

7 Claims, No Drawings

N-METHANESULFONIC ACID DERIVATIVES OF 3-DEMETHOXYISTAMYCIN B

SUMMARY OF THE INVENTION

This invention relates to a less toxic derivative of 3-demethoxyistamycin B which is a new compound or substance useful for therapeutic treatment of bacterial infections. More particularly, this invention relates to a new N-methanesulfonic acid derivative of 3-demethoxyistamycin B and also to a process for the production of said derivative.

BACKGROUND OF THE INVENTION

Istamycin $B_o$ is an aminoglycosidic antibiotic which was discovered by the present inventors and is produced in the culture broth of *Streptomyces tenjimariensis* (see Japanse patent application prepublication "Kokai" No. 43295/81; U.K. Pat. No. 2048855; and U.S. Pat. No. 4296106). 3-Demethoxyistamycin B is a new semi-synthetic aminoglycosidic antibiotic which was synthesized by us from istamycin $B_o$ and exhibits a high antibacterial activity against a wide range of gram-negative and gram-positive bacteria, including *Pseudomonas aeruginosa* (see Japanse Patent application No. 193436/82; EPC patent application No. 83306537.8; and U.S. patent application Ser. No. 545,686). 3-Demethoxyistamycin B is represented by the formula

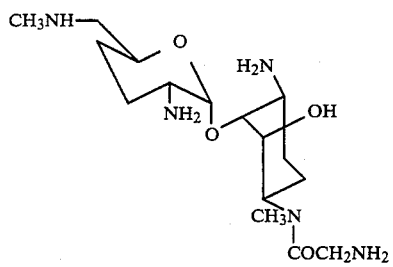

It is known that a few of aminoglycosidic antibiotic substances are converted into an N-methanesulfonic acid derivative thereof by N-sulfomethylation of some or all of the amino group(s) present in the antibiotic molecule, and that the N-methanesulfonic acid derivative so produced exhibits a lower toxicity than the parent antibiotic. An example is N-methanesulfonic acid derivatives of kanamycin A (Journal of Antibiotics, A 14, page 170 (1961)). Besides, it has been found by the present invention that an N-methanesulfonic acid derivative of 3',4'-dideoxykanamycin B can be synthesized by reaction of 3',4'-dideoxykanamycin B, an aldehyde and sulfurous acid or an alkali metal hydrogen sulfite with each other, and that this N-methanesulfonic acid derivative is of lower toxicity than the parent 3',4'-dideoxykanamycin B and hence is valuable for therapeutic treatment of bacterial infections (see Japanese patent application prepublication "Kokai" No. 39653/77; U.K. Pat. No. 1507118; U.S. Pat. No. 4,091,202). It has also been found by us that an N-methanesulfonic acid derivative of istamycin A or B and that of 3-0-demethylistamycin B may be obtained as new less toxic substances having useful antibacterial activity (see Japanese patent application prepublication "Kokai" No. 40496/82; published U.K. patent application GB 2083464A; U.S. patent application Ser. No. 289,963 for the former and Japanese patent application prepublication "Kokai" No. 128395/83; U.S. patent application Ser. No. 458,824 for the latter).

The discoveries mentioned above are solely related to N-methanesulfonic acid derivatives of kanamycin, istamycins A and B and 3-0-demethylistamycin B and are not extensively applicable to those of all the aminoglycosidic antibiotics.

An object of this invention is to provide a new antibiotic derivative of 3-demethoxyistamycin B which, we have found, retains useful antibacterial activity of 3-demethoxyistamycin B but exhibits a lower toxicity than that of 3-demethoxyistamycin B itself. The other object is to provide a process for the preparation of such new antibiotic derivative of 3-demethoxyistamycin B. Another objects of this invention will be clear from the following descriptions.

As a result of our research, we have now found that as new compounds or substances, N-methanesulfonic acid derivatives of 3-demethoxyistamycin B can be synthesized by reaction of 3-demethoxyistamycin B of the above formula (I) or a partial acid addition salt thereof with an aldehyde of the formula:

wherein R is as defined later and also with sulfurous acid or an alkali or alkaline earth metal hydrogen sulfite or ammonium hydrogen sulfite of the formula:

wherein M is a hydrogen atom, an alkali metal, alkaline earth metal atom or ammonium cation. We have confirmed that these N-methanesulfonic acid derivatives of 3-demethoxyistamycin B are of remarkedly lower toxicity than 3-demethoxyistamycin B itself. 3-Demethoxyistamycin B contains three amino groups and one methylamino group per molecule as will be clear from the above formula (I), and it has been found that the new N-methanesulfonic acid derivative of 3-demethoxyistamycin B so prepared is such one in which one, two, three or four groups of the aforesaid three amino groups and one methylamino group present in the molecule has or have been N-sulfomethylated, that is to say, substituted with a methanesulfonate group of the formula:

wherein R is a hydrogen atom, an alkyl group, preferably an alkyl group of 1-4 carbon atoms, a substituted alkyl group, a phenyl group or a substituted phenyl group, and M represents a hydrogen atom, an ammonium cation, an alkali metal or an alkaline earth metal atom. The total number of the N-sulfomethylated amino and methylamino groups present in the resulting N-methanesulfonic acid derivative of 3-demethoxyistamycin B amounts to 1, 2, 3 or 4, depending upon the molar proportions of the aldehyde and the sulfurous acid or sulfite compound employed for 1 molar proportion of 3-demethoxyistamycin B.

DETAILED DESCRIPTION OF THE INVENTION

According to a first aspect of this invention, there is provided as a new compound or substance, an N-methanesulfonic acid derivative of 3-demethoxyistamycin B of the formula:

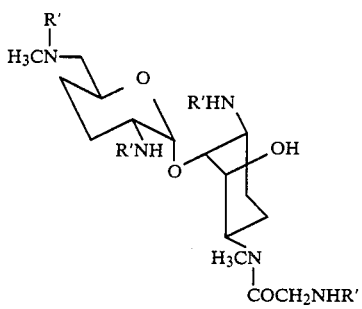

(III)

wherein one, two, three or four of the R' groups denote(s) each a group —CHRSO₃M and the remaining other R' group(s) denote(s) each a hydrogen atom, where R is a hydrogen atom, an alkyl group, a substituted alkyl group, a phenyl group or a substituted phenyl group, and M is a hydrogen atom, an ammonium cation, an alkali metal atom or an alkaline earth metal atom.

When R in the group —CHRSO₃M shown above denotes an alkyl group, it may preferably be a lower alkyl containing 1 to 4 carbon atoms, such as methyl, ethyl, n-propyl and n-butyl. R may also be a substituted alkyl group such as a lower alkyl bearing one or more methoxy or chloro substituents thereon. Suitable examples of the substituted alkyl group include methoxymethyl, monochloromethyl and dichloromethyl. When R is a substituted phenyl group, it may be, for example, p-methoxyphenyl and o-hydroxyphenyl. According to a particular embodiment of the first aspect invention, there is provided an N-methanesulfonic acid derivative of 3-demethoxyistamycin B which is selected from (1) 3-demethoxyistamycin B-mono-N-methanesulfonic acid sodium salt, namely the compound of the formula (III) where one R' group is a group —CHRSO₃M, the remaining three R' groups are each a hydrogen atom, R is a hydrogen atom and M is sodium; (2) 3-demethoxyistamycin B-di-N-methanesulfonic acid sodium salt, namely the compound of the formula (III) where two R' grops are each a group —CHRSO₃M, the remaining two R' groups are each a hydrogen atom, R is a hydrogen atom and M is sodium; (3) 3-demethoxyistamycin B-tri-N-methane sulfonic acid sodium salt, namely the compound of the formula (III) where three R' groups are each a group —CHRSO₃M, the remaining one R' group is a hydrogen atom, R is a hydrogen atom and M is sodium; and (4) 3-demethoxyistamycin B-tetra-N-methanesulfonic acid sodium salt, namely the compound of the formula (III) where all four R' groups are each a group —CHRSO₃M, R is a hydrogen atom and M is sodium.

Particular examples of the N-methanesulfonic acid derivative of 3-demethoxyistamycin B obtained according to this invention are listed below together with physicochemical properties thereof:

(1) 3-Demethoxyistamycin B-mono-N-methanesulfonic acid sodium salt of the formula $C_{16}H_{32}N_5O_4(CH_2SO_3Na)$. This substance is in the form of a colorless powder which has no definite melting point, decomposes gradually above 210° C. and shows a specific optical rotation $[\alpha]_D^{23}+49°$ (c 1, water).

Elemental analysis: Found: S 7.40%; Calcd.: S 6.74%.

(2) 3-Demethoxyistamycin B-di-N-methanesulfonic acid sodium salt of the formula $C_{16}H_{31}N_5O_4(CH_2SO_3Na)_2$. This substance is in the form of a colorless powder which has no definite melting point, decomposes gradually at 248° C. and shows a specific optical rotation $[\alpha]_D^{23}+47°$ (c 1, water).

Elemental analysis: Found: S 11.12%; Calcd.: S 10.84%.

(3) 3-Demethoxyistamycin B-tri-N-methanesulfonic acid sodium salt of the formula $C_{16}H_{30}N_5O_4(CH_2SO_3Na)_3$. This substance is in the form of a colorless powder which has no definite melting point, decomposes gradually at 238° C. and shows a specific optical rotation $[\alpha]_D^{23}+46°$ (c 1, water).

Elemental analysis: Found: S 13.24%; Calcd. S 13.59%.

(4) 3-Demethoxyistamycin B-tetra-N-methanesulfonic acid sodium salt of the formula $C_{16}H_{29}N_5O_4(CH_2SO_3Na)_4$. This compound is also in the form of a colorless powder which has no definite melting point, decomposes gradually at 219° C. and shows a specific optical rotation $[\alpha]_D^{23}+45°$ (c 1, water).

Elemental analysis: Found: S 14.54%; Calcd.: S 15.57%.

According to a particular embodiment of this invention, therefore, there is provided an N-methanesulfonic acid derivative of 3-demethoxyistamycin B of the formula:

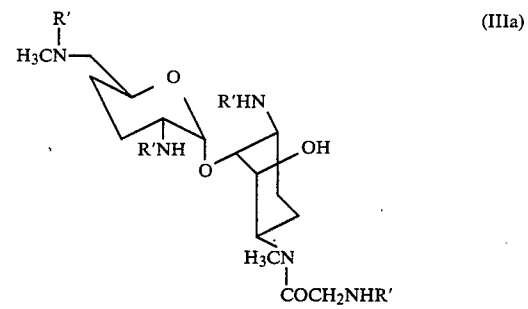

(IIIa)

wherein one, two, three or four of the R' groups denote(s) each a group —CH₂SO₃M' and the remaining other R' group(s) denotes each a hydrogen atom, where M' is an alkali metal atom, an alkaline earth metal or ammonium cation.

Each of the above-mentioned particular 3-demethoxyistamycin B N-methanesulfonic acid derivatives is readily soluble in water but little soluble or insoluble in a lower alkanol such as methanol, ethanol and 1-butanol, tetrahydrofuran, dioxane and N,N-dimethylformamide.

The new compounds or substances of this invention exhibit high antibacterial activity against a variety of gram-negative and gram-positive bacteria, including *Pseudomonas aeruginosa*, as will be clear from antibacterial spectra of them shown in Table 1 below, wherein there are set out the minimum inhibitory concentrations (mcg/ml) of 3-demethoxyistamycin B-mono-N-methanesulfonic acid sodium salt [abbreviated as Compound (1)]; 3-demethoxyistamycin B-di-N-methanesulfonic acid sodium salt [abbreviated as Compound (2)]; 3-demethoxyistamycin B-tri-N-methanesulfonic acid sodium salt [abbreviated as Compound (3)]; and 3-demethoxyistamycin B-tetra-N-methanesulfonic acid sodium salt [abbreviated as Compound (4)] of this invention against various bacteria which have been estimated according to a standard serial dilution method using Mueller-Hinton agar as the incubation medium, the incubation being made at 37° C. for 17 hours. Minimum inhibitory concentrations (mcg/ml) of the parent 3-demethoxyistamycin B were also estimated in the same manner for the comparison purpose and also are shown in Table 1.

TABLE 1

| | Minimum Inhibitory concentrations (mcg/ml) | | | | |
|---|---|---|---|---|---|
| Test Microorganism | Compound (1) | Compound (2) | Compound (3) | Compound (4) | 3-Demethoxy-istamycin B (comparative) |
| *Staphylococcus aureus* 209P | 0.78 | 0.78 | 1.56 | 1.56 | <0.20 |
| *Staphylococcus aureus* Ap01 | 1.56 | 0.78 | 0.78 | 1.56 | 0.39 |
| *Escherichia coli* K-12 | 1.56 | 1.56 | 1.56 | 1.56 | 0.78 |
| *Escherichia coli* K-12 R5 | 6.25 | 3.13 | 3.13 | 6.25 | 1.56 |
| *Escherichia coli* K-12 ML1629 | 1.56 | 1.56 | 1.56 | 3.13 | 0.78 |
| *Escherichia coli* K-12 LA290 R55 | 3.13 | 1.56 | 1.56 | 3.13 | 1.56 |
| *Escherichia coli* JR66/W677 | 6.25 | 3.13 | 3.13 | 6.25 | 0.78 |
| *Escherichia coli* K-12 C600 R135 | 6.25 | 6.25 | 6.25 | 6.25 | 0.78 |
| *Escherichia coli* JR225 | 1.56 | 1.56 | 1.56 | 1.56 | 0.78 |
| *Serratia marcescens* | 6.25 | 3.13 | 6.25 | 3.13 | 0.78 |
| *Providencia* Pv 16 | 3.13 | 1.56 | 3.13 | 1.56 | 0.78 |
| *Pseudomonas aeruginosa* A3 | 0.78 | 0.78 | 0.78 | 1.56 | 0.39 |
| *Pseudomonas aeruginosa* H9 | 50 | 50 | 50 | 50 | 12.5 |
| *Pseudomonas aeruginosa* TI-13 | 25 | 25 | 25 | 25 | 6.25 |
| *Pseudomonas aeruginosa* GN315 | 100 | 100 | 50 | 25 | 6.25 |

The N-methanesulfonic acid derivatives of 3-demethoxyistamycin B according to this invention have a remarkedly reduced acute toxicity, as compared with the parent 3-demethoxyistamycin B, notwithstanding that the former compounds or substances of this invention retain high antibacterial activity against various bacteria.

Acute toxicity of the various N-methanesulfonic acid derivatives of 3-demethoxyistamycin B of the invention has been determined by the following procedure:

A test compound or substance was dissolved in 0.25 ml of a physiological saline solution and the solution of the test compound or substance so prepared was intravenously administered into a series of mouse groups each consisting of six mice (ICR strain, adult female, body weight 20 g±0.5 g) as the test animal, so that the test compound or substance was given to each mouse. Acute toxicity of 3-demethoxyistamycin B was also estimated in the same manner as above for the comparison purpose. It was then observed that all mice survived for more than 14 days when the N-methanesulfonic acid derivatives of 3-demethoxyistamycin B were administered at a dosage of 500 mg/kg (LD$_{50}$ more than 500 mg/kg), whereas 3-demethoxyistamycin B (comparative) showed LD$_{50}$ of 100–200 mg/kg.

From the test results of Table 1 and of acute toxicity as mentioned above, it is evident that the new compounds or substances of the invention have remarkedly reduced toxicity but retain usefully high antibacterial activity against various bacteria.

The new compounds or substances of the invention are effective in the treatment of bacterial infections when administered intramuscularly in the dosage range of about 100 mg to about 1000 mg per day in divided doses twice to four times a day. Generally, the new compounds or substances may be administered orally, intraperitoneally, intravenously or intramuscularly using any pharmaceutical form known to the art for such administration and in a similar manner to kanamycins. Examples of pharmaceutical forms for oral administration are powders, capsules, tablets, syrup and the like.

The new N-methanesulfonic acid derivatives of 3-demethoxyistamycin B of the above formula (III) according to the invention may be prepared by reaction of 3-demethoxyistamycin B, either in the form of the free base or a partially acid-addition salt thereof, with an aldehyde of the formula:

RCHO  (IV)

wherein R is a hydrogen atom, an alkyl group, particularly a lower alkyl group of 1–4 carbon atoms, a substituted alkyl group, a phenyl group or a substituted phenyl group, and sulfurous acid or a sulfite of the formula:

MHSO$_3$  (V)

wherein M is a hydrogen atom, an ammonium cation, an alkali metal atom or an alkaline earth metal atom. The resulting N-methanesulfonic acid derivative contains a certain number of N-methanesulfonate group(s) which takes 1, 2, 3 or 4 depending upon the molar proportions of the aldehyde and the sulfurous acid or sulfite compound employed for 1 molar porportion of 3-demethoxyistamycin B. The aldehyde and the sulfurous acid or sulfite may be reacted simultaneously with 3-demethoxyistamycin B, or alternatively either one of the aldehyde reagent and the sulfurous acid or sulfite reagent may be first reacted with 3-demethylistamycin B before the resulting reaction product is reacted with the other reagent.

According to a second aspect of this invention, therefore, there is provided a process for the preparation of an N-methanesulfonic acid derivative of 3-demethoxyistamycin B of the formula

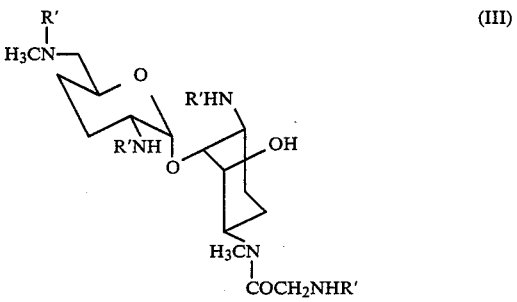

(III)

wherein one, two, three or four of the R' groups denote(s) each a group —CHRSO$_3$M and the remaining other R' group(s) denote(s) each a hydrogen atom, where R is a hydrogen atom, an alkyl group, a substituted alkyl group, a phenyl group or a substituted phenyl group, and M is a hydrogen atom, an ammonium cation, an alkali metal atom or an alkaline earth metal atom, which comprises reacting 3-demethoxyistamycin B or a partial acid addition salt thereof with an aldehyde of the formula

RCHO         (IV)

wherein R is as defined above, and sulfurous acid or a sulfite of the formula

MHSO$_3$         (V)

wherein M is as defined above.

When sulfurous acid of the above formula (V) where M is a hydrogen atom is used as one of the reagents in the process of the invention, it may conveniently be used in the form of gaseous sulfur dioxide. However, it is feasible, of course, to employ aqueous sulfurous acid. Instead of the sulfurous acid reagent, an alkali metal, alkaline earth metal or ammonium hydrogen sulfite may be used as an equivalent agent. Sodium hydrogen sulfite, potassium hydrogen sulfite, lithium hydrogen sulfite and ammonium hydrogen sulfite are suitable as the sulfite for the purpose of the invention. Suitable examples of the aldehyde reagent of the formula (IV) available for the invention include paraformaldehyde, acetaldehyde, methoxyacetaldehyde, monochloroacetaldehyde, dichloroacetaldehyde, glyoxal, propionaldehyde, n-butylaldehyde, benzaldehyde, p-methoxybenzaldehyde and salicylaldehyde.

In preparing the new compound of the above formula (III) according to the invention, either one of the aldehyde reagent of the formula (IV) and the sulfurous acid or sulfite reagent of the formula (V) may be first reacted with 3-demethoxyistamycin B. Thus, it is feasible to carry out the process in such a manner that the aldehyde reagent is first reacted with 3-demethoxyistamycin B to produce the corresponding Schiff's base and the Schiff's base so formed is isolated and then reacted with the sulfurous acid or sulfite reagent to yield the desired 3-demethoxyistamycin B N-methanesulfonic acid derivative (III) as the final product. Alternatively, it is possible to conduct the process in such a manner that the sulfurous acid or sulfite reagent is first reacted with 3-demethoxyistamycin B to convert the latter into the form of an acid-addition salt with sulfurous acid, which is subsequently reacted with the aldehyde reagent to yield the desired N-methanesulfonic acid derivative (III) as the final product. Moreover, an adduct of both the reagents (IV) and (V) such as sodium hydroxymethanesulfonate or glyoxal sodium hydrogen sulfite may also be used in the process of the invention. Namely, this adduct may be directly reacted with 3-demethoxyistamycin B to yield the desired N-methanesulfonic acid derivative (III) as the final product.

As will be clear from the above, the molar proportions of the aldehyde reagent and the sulfurous acid or sulfite reagent to be interacted with 3-demethoxyistamycin B may vary from 1 molar to 4 molar proportions for 1 molar proportion of 3-demethoxyistamycin B. The N-methanesulfonic acid derivatives obtained as the final product by the process of the invention contain the methanesulfonate component at different contents depending on the molar proportions of the aldehyde reagent and the sulfurous acid or sulfite reagent employed, but they usually contain one, two, three or four N-methanesulfonate groups per molecule of 3-demethoxyistamycin B.

Generally, the process may be carried out preferably in water as the reaction medium, but a small proportion of a lower alcohol such as methanol and ethanol may be added to the reaction medium when the starting aldehyde (IV) is hardly soluble in water. The process may readily be conducted at a temperature of 0° to 70° C. usually for a reaction period of 0.5 to 24 hours.

For recovery of the final product from the reaction solution, it may be precipitated as a colorless deposit by adding thereto a volume of an organic solvent in which the desired product is sparingly soluble, such as a lower alcohol, e.g. methanol and ethanol, tetrahydrofuran, dioxane and N,N-dimethylformamide. The precipitate so formed is filtered out, washed with methanol or ethanol and then dried to afford the desired 3-demethoxyistamycin B N-methanesulfonic acid derivative (III) in a good yield.

As stated before, the new compounds or substances of the invention are effective in treatment of bacterial infections. According to a third aspect of the invention, therefore, there is provided an antibacterial pharmaceutical composition comprising an antibacterially effective amount of a 3-demethoxyistamycin B N-methanesulfonic acid derivative of the formula (III), in combination with a pharmaceutically acceptable carrier therefor.

The invention is now illustrated with reference to the following Examples which are in no way limitative for the invention.

EXAMPLE 1

3-Demethoxyistamycin B (free base) (100 mg; 0.28 millimoles) was dissolved in water (1.0 ml), and the resultant aqueous solution was admixed with sodium hydrogen sulfite (29 mg; 0.28 millimoles) and paraformaldehyde (8.5 mg; 0.28 millimoles). The mixture obtained was shaken at ambient temperature overnight for the reaction. Ethanol (10 ml) was added to the reaction solution to deposit a colorless precipitate. This precipitate was collected by filtration and dried under reduced pressure to a constant weight, affording 55 mg of a colorless powder of 3-demethoxyistamycin B-mono-N-methanesulfonic acid sodium salt which gradually decomposed above 210° C. $[\alpha]_D^{23}+49°$ (c 1, water).

EXAMPLE 2

3-Demethoxyistamycin B (free base) (100 mg; 0.28 millimoles) was dissolved in water (1.0 ml), and the resultant aqueous solution was admixed with sodium hydrogen sulfite (58 mg; 0.56 millimoles) and paraformaldehyde (17 mg; 0.56 millimoles). The mixture obtained was shaken at ambient temperature overnight for the reaction. Ethanol (10 ml) was added to the reaction solution to deposit a colorless precipitate. This precipitate was collected by filtration and dried under reduced pressure to a constant weight, affording 95 mg of a colorless powder of 3-demethoxyistamycin B-di-N-methanesulfonic acid sodium salt which decomposed gradually at 248° C. $[\alpha]_D^{23}+47°$ (c 1, water).

EXAMPLE 3

3-Demethoxyistamycin B (free base) (100 mg; 0.28 millimoles) was dissolved in water (1.5 ml), and the resultant aqueous solution was admixed with sodium hydrogen sulfite (87 mg; 0.84 millimoles) and paraformaldehyde (25 mg; 0.84 millimoles). The mixture obtained was shaken at ambient temperature overnight for the reaction. Ethanol (12.5 ml) was added to the reaction solution to deposit a colorless precipitate. This precipitate was collected by filtration and dried under reduced pressure to a constant weight, affording 153 mg of a colorless powder of 3-demethoxyistamycin B-tri-N-methanesulfonic acid sodium salt which decomposed gradually at 238° C. $[\alpha]_D^{23} +46°$ (c 1, water).

EXAMPLE 4

3-Demethoxistamycin B (free base) (100 mg; 0.28 millimoles) was dissolved in water (2.0 ml), and the resultant aqueous solution was admixed with sodium hydrogen sulfite (116 mg; 1.12 millimoles) and paraformaldehyde (34 mg; 1.12 millimoles). The mixture obtained was shaken at ambient temperature overnight for the reaction. Ethanol (15 ml) was added to the reaction solution to deposit a colorless precipitate. This precipitate was collected by filtration and dried under reduced pressure to a constant weight, affording 177 mg of a colorless powder of 3-demethoxyistamycin B-tetra-N-methanesulfonic acid sodium salt which decomposed gradually at 219° C. $[\alpha]_D^{23} +45°$ (c 1, water).

We claim:

1. An N-methanesulfonic acid derivative of 3-demethoxyistamycin B represented by the formula

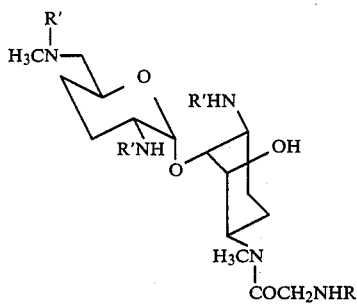

(III)

wherein one, two, three or four of the R' groups denote(s) each a group —CHRSO₃M and the remaining other R' group(s) denote(s) each a hydrogen atom, where R is a hydrogen atom, an alkyl group, a phenyl group, and M is a hydrogen atom, an ammonium cation, an alkali metal atom or an alkaline earth metal atom.

2. An N-methanesulfonic acid derivative of 3-demethoxyistamycin B of the formula

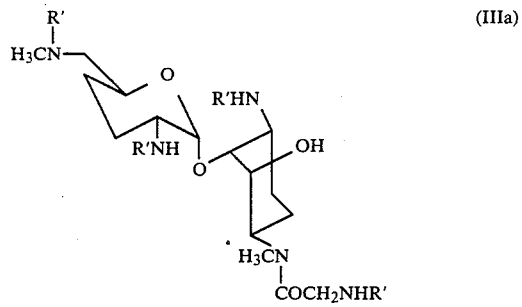

(IIIa)

wherein one, two, three or four of the R' groups denote(s) each a group —CH₂SO₃M' and the remaining other R' group(s) denote(s) each a hydrogen atom, where M' is an alkali metal, an alkaline earth metal or an ammonium cation.

3. A derivative according to claim 1 which is 3-demethoxyistamycin B-mono-N-methanesulfonic acid sodium salt, the compound of the formula (III) where one R' group is a group —CHRSO₃M and the remaining three R' groups are each a hydrogen atom; and R is a hydrogen atom and M is sodium.

4. A derivative according to claim 1 which is 3-demethoxyistamycin B-di-N-methanesulfonic acid sodium salt, the compound of the formula (III) where two R' groups are each a group —CHRSO₃M and the remaining two R' groups are each a hydrogen atom; and R is a hydrogen atom and M is sodium.

5. A derivative according to claim 1 which is 3-demethoxyistamycin B-tri-N-methanesulfonic acid sodium salt, the compound of the formula (III) where three R' groups are each a group —CHRSO₃M and the remaining one R' group is a hydrogen atom; and R is a hydrogen atom and M is sodium.

6. A derivative according to claim 1 which is 3-demethoxyistamycin B-tetra-N-methanesulfonic acid sodim salt, the compound of the formula (III) where all four R' groups are each a group —CHRSO₃M and R is a hydrogen atom and M is sodium.

7. An antibacterial pharmaceutical composition comprising an antibacterially effective amount of a derivative according to claim 1, in combination with a pharmaceutically acceptable carrier therefor.

* * * * *